United States Patent
Pandey (10) Patent No.: US 10,067,426 B2
(45) Date of Patent: Sep. 4, 2018

(54) METROLOGY APPARATUS FOR MEASURING A STRUCTURE FORMED ON A SUBSTRATE BY A LITHOGRAPHIC PROCESS, LITHOGRAPHIC SYSTEM, AND METHOD OF MEASURING A STRUCTURE FORMED ON A SUBSTRATE BY A LITHOGRAPHIC PROCESS

(71) Applicant: ASML Netherlands B.V., Veldhoven (NL)

(72) Inventor: Nitesh Pandey, Eindhoven (NL)

(73) Assignee: ASML Netherlands B.V., Veldhoven (NL)

(*) Notice: Subject to any disclaimer, the term of this patent is extended or adjusted under 35 U.S.C. 154(b) by 0 days.

(21) Appl. No.: 15/683,126

(22) Filed: Aug. 22, 2017

(65) Prior Publication Data
US 2018/0059552 A1     Mar. 1, 2018

(30) Foreign Application Priority Data

Aug. 23, 2016 (EP) .................................... 16185319

(51) Int. Cl.
*G03B 27/72* (2006.01)
*G03B 27/42* (2006.01)
(Continued)

(52) U.S. Cl.
CPC ........ *G03F 7/70633* (2013.01); *G01J 1/0411* (2013.01); *G01J 1/0488* (2013.01); *G03F 7/70191* (2013.01); *G03F 7/70575* (2013.01)

(58) Field of Classification Search
CPC ... G01J 1/0411; G01J 1/0488; G03F 7/70191; G03F 7/7015; G03F 7/7055;
(Continued)

(56) References Cited

U.S. PATENT DOCUMENTS 7,663,753 B2* 2/2010 Mieher ................ G01N 21/956
356/401
2006/0066855 A1 3/2006 Boef et al.
(Continued)

FOREIGN PATENT DOCUMENTS

EP     0 498 541 A1     8/1992
EP     1 628 164 A2     2/2006
(Continued)

OTHER PUBLICATIONS

International Search Report and Written Opinion of the International Searching Authority directed to related International Patent Application PCT/EP2017/070302, dated Nov. 15, 2017; 13 pages.
(Continued)

*Primary Examiner* — Christina Riddle
(74) *Attorney, Agent, or Firm* — Sterne, Kessler, Goldstein & Fox P.L.L.C.

(57) ABSTRACT

Metrology apparatus and methods are disclosed. In one arrangement, a metrology apparatus comprises an optical system that illuminates a structure with measurement radiation and detects the measurement radiation scattered by the structure. The optical system comprises an array of lenses that focuses the scattered measurement radiation onto a sensor. A dispersive element directs scattered measurement radiation in each of a plurality of non-overlapping wavelength bands exclusively onto a different respective lens of the array of lenses.

20 Claims, 6 Drawing Sheets

(51) Int. Cl.
*G03F 7/20* (2006.01)
*G01J 1/04* (2006.01)

(58) Field of Classification Search
CPC ............. G03F 7/70575; G03F 7/70583; G03F 7/70616; G03F 7/70633; G03F 7/70666–7/70683; G03F 7/7085; G03F 9/7007
USPC ....... 356/300, 302, 326, 330, 614–616, 620, 356/399–401; 355/52, 53, 55, 67–71, 355/72–75, 77; 250/492.1, 492.2, 492.22
See application file for complete search history.

(56) References Cited

U.S. PATENT DOCUMENTS

| 2008/0068609 | A1 | 3/2008 | Werkman et al. |
| 2011/0027704 | A1 | 2/2011 | Cramer et al. |
| 2011/0043791 | A1 | 2/2011 | Smilde et al. |
| 2012/0242970 | A1 | 9/2012 | Smilde et al. |
| 2015/0077764 | A1* | 3/2015 | Braker ............... G01B 11/2518 356/620 |
| 2017/0097575 | A1* | 4/2017 | Pandey ................ G01B 11/272 |
| 2017/0219487 | A1* | 8/2017 | Hill ........................ G02B 27/10 |

FOREIGN PATENT DOCUMENTS

| JP | 2002-372406 A | 12/2002 |
| WO | WO 2009/078708 A1 | 6/2009 |
| WO | WO 2009/106279 A1 | 9/2009 |

OTHER PUBLICATIONS

Taiwanese Office Action with English-language machine translation attached, dated May 14, 2018; 8 pages.

* cited by examiner

METROLOGY APPARATUS FOR MEASURING A STRUCTURE FORMED ON A SUBSTRATE BY A LITHOGRAPHIC PROCESS, LITHOGRAPHIC SYSTEM, AND METHOD OF MEASURING A STRUCTURE FORMED ON A SUBSTRATE BY A LITHOGRAPHIC PROCESS

FIELD

The present invention relates to a metrology apparatus for measuring a structure formed on a substrate by a lithographic process, a lithographic system, and a method of measuring a structure formed on a substrate by a lithographic process.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. In lithographic processes, it is desirable frequently to make measurements of the structures created, e.g., for process control and verification. Various tools for making such measurements are known, including scanning electron microscopes, which are often used to measure critical dimension (CD), and specialized tools to measure overlay, a measure of the accuracy of alignment of two layers in a device. Overlay may be described in terms of the degree of misalignment between the two layers, for example reference to a measured overlay of 1 nm may describe a situation where two layers are misaligned by 1 nm.

Recently, various forms of scatterometers have been developed for use in the lithographic field. These devices direct a beam of radiation onto a target and measure one or more properties of the scattered radiation—e.g., intensity at a single angle of reflection as a function of wavelength; intensity at one or more wavelengths as a function of reflected angle; or polarization as a function of reflected angle—to obtain a "spectrum" from which a property of interest of the target can be determined. Determination of the property of interest may be performed by various techniques: e.g., reconstruction of the target by iterative approaches such as rigorous coupled wave analysis or finite element methods; library searches; and principal component analysis.

The targets used by conventional scatterometers are relatively large, e.g., 40 µm by 40 µm, gratings and the measurement beam generates a spot that is smaller than the grating (i.e., the grating is underfilled). This simplifies mathematical reconstruction of the target as it can be regarded as infinite. However, in order to reduce the size of the targets, e.g., to 10 µm by 10 µm or less, e.g., so they can be positioned in amongst product features, rather than in the scribe lane, metrology has been proposed in which the grating is made smaller than the measurement spot (i.e., the grating is overfilled). Typically such targets are measured using dark field scatterometry in which the zeroth order of diffraction (corresponding to a specular reflection) is blocked, and only higher orders processed. Examples of dark field metrology can be found in international patent applications WO 2009/078708 and WO 2009/106279 which documents are hereby incorporated by reference in their entirety. Further developments of the technique have been described in patent publications US20110027704A, US20110043791A and US20120242970A. The contents of all these applications are also incorporated herein by reference. Diffraction-based overlay using dark-field detection of the diffraction orders enables overlay measurements on smaller targets. These targets can be smaller than the illumination spot and may be surrounded by product structures on a wafer. Targets can comprise multiple gratings which can be measured in one image.

In the known metrology technique, overlay measurement results are obtained by measuring an overlay target twice under certain conditions, while either rotating the overlay target or changing the illumination mode or imaging mode to obtain separately the $-1^{st}$ and the $+1^{st}$ diffraction order intensities. The intensity asymmetry, a comparison of these diffraction order intensities, for a given overlay target provides a measurement of target asymmetry, that is asymmetry in the target. This asymmetry in the overlay target can be used as an indicator of overlay error (undesired misalignment of two layers).

Metrology apparatuses, when performing such dark field scatterometry, presently can only perform measurements using measurement radiation of a single wavelength at any one time. However, different targets in different layers may show different behavior to different wavelength measurement radiation, which can result in variable measurement quality. Variations as a function of wavelength may also arise due to processing induced changes to the target structure. For example, semiconductor manufacturing processes such as Chemical Mechanical Planarization etching and non-uniformity of layer thickness variations change the structure of the metrology target and hence also the optimum wavelength. It is therefore desirable for measurement radiation to be individually tuned to a target and/or layer.

SUMMARY

It is desirable to provide metrology apparatus and methods that allow high quality measurements to be performed efficiently.

According to an aspect of the invention, there is provided a metrology apparatus for measuring a structure formed on a substrate by a lithographic process, the metrology apparatus comprising: an optical system configured to illuminate the structure with measurement radiation and detect the measurement radiation scattered by the structure, the optical system comprising: an array of lenses configured to focus the scattered measurement radiation onto a sensor; and a dispersive element configured to direct scattered measurement radiation in each of a plurality of non-overlapping wavelength bands exclusively onto a different respective lens of the array of lenses.

According to an aspect of the invention, there is provided a method of measuring a structure formed on a substrate by a lithographic process, comprising: illuminating the structure with measurement radiation comprising at least a plurality of non-overlapping wavelength bands; using a dispersive element to spectrally disperse the measurement radiation after scattering of the measurement radiation by the structure in order to direct scattered measurement radiation from each of the plurality of non-overlapping wavelength bands exclusively onto a different respective lens of an array of lenses; and detecting radiation from each lens of the array of lenses on a sensor.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION OF EXEMPLARY EMBODIMENTS

This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment," "an embodiment," "an example embodiment," etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Before describing such embodiments in more detail, however, it is instructive to present an example environment in which embodiments of the present invention may be implemented.

Figure 1:
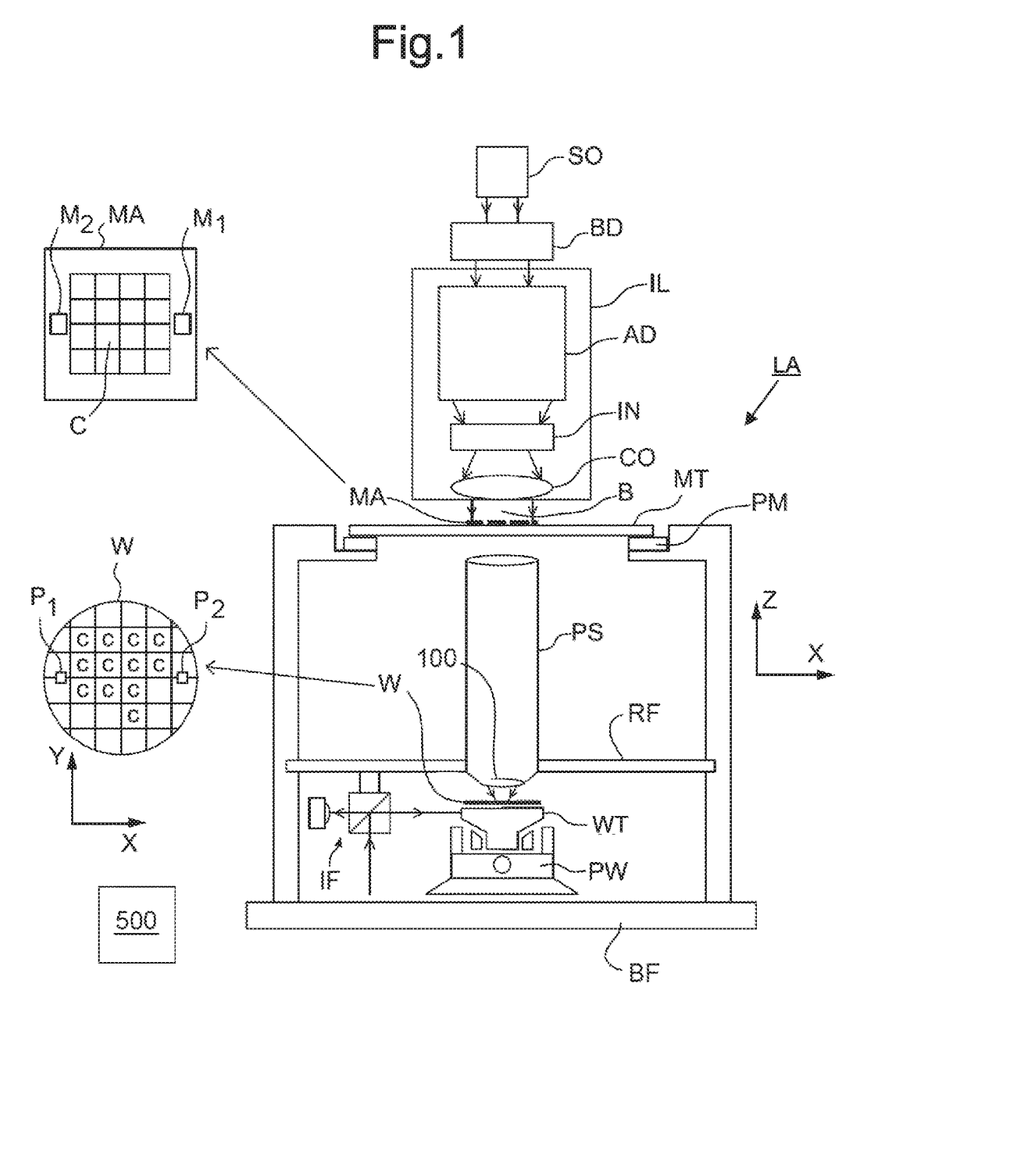
FIG. 1 depicts a lithographic apparatus.

FIG. 1 schematically depicts a lithographic apparatus LA. The apparatus includes an illumination system (illuminator) IL configured to condition a radiation beam B (e.g., UV radiation or DUV radiation), a support structure (e.g., a mask table) MT constructed to support a patterning device (e.g., a mask) MA and connected to a first positioner PM configured to accurately position the patterning device in accordance with certain parameters, a substrate table (e.g., a wafer table) WT constructed to hold a substrate (e.g., a resist coated wafer) W and connected to a second positioner PW configured to accurately position the substrate in accordance with certain parameters, and a projection system (e.g., a refractive projection lens system) PS configured to project a pattern imparted to the radiation beam B by patterning device MA onto a target portion C (e.g., comprising one or more dies) of the substrate W.

The illumination system may include various types of optical components, such as refractive, reflective, magnetic, electromagnetic, electrostatic, or other types of optical components, or any combination thereof, for directing, shaping, or controlling radiation.

The support structure supports, i.e., bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing various types of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system."

In this embodiment, for example, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (dual stage) or more substrate tables and, for example, two or more mask tables. In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (which are commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam to have a desired uniformity and intensity distribution in its cross section.

The radiation beam B is incident on the patterning device (e.g., mask MA), which is held on the support structure (e.g., mask table MT), and is patterned by the patterning device. Having traversed the mask MA, the radiation beam B passes through the projection system PS, which focuses the beam onto a target portion C of the substrate W. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the mask MA with respect to the path of the radiation beam B, e.g., after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e., a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e., a single dynamic exposure). The velocity and direction of the substrate table WT relative to the mask table MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
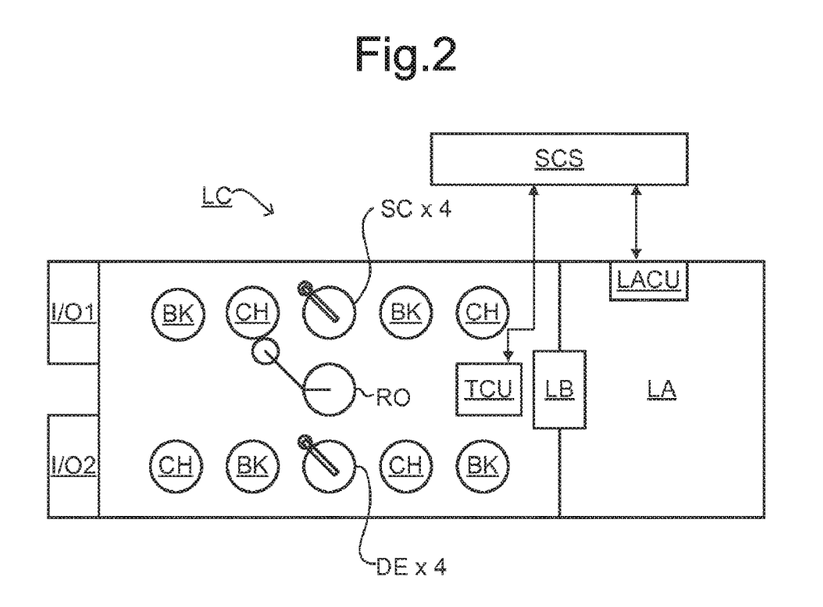
FIG. 2 depicts a lithographic cell or cluster.

As shown in FIG. 2 the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU that is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. If errors are detected, adjustments, for example, can be made to exposures of subsequent substrates, especially if the inspection can be done soon and fast enough that other substrates of the same batch are still to be exposed. Also, already exposed substrates may be stripped and reworked to improve yield, or possibly be discarded, thereby avoiding performing exposures on substrates that are known to be faulty. In a case where only some target portions of a substrate are faulty, further exposures can be performed only on those target portions that are deemed to be non-faulty.

A metrology apparatus is used to determine the properties of the substrates, and in particular, how the properties of different substrates or different layers of the same substrate vary from layer to layer. The metrology apparatus may be integrated into the lithographic apparatus LA or the lithocell LC or may be a stand-alone device. To enable most rapid measurements, it is desirable that the metrology apparatus measure properties in the exposed resist layer immediately after the exposure. However, the latent image in the resist has a very low contrast, as in there is only a very small difference in refractive index between the parts of the resist which have been exposed to radiation and those which have not—and not all metrology apparatus have sufficient sensitivity to make useful measurements of the latent image. Therefore measurements may be taken after the post-exposure bake step (PEB) that is customarily the first step carried out on exposed substrates and increases the contrast between exposed and unexposed parts of the resist. At this stage, the image in the resist may be referred to as semi-latent. It is also possible to make measurements of the developed resist image, at which point either the exposed or unexposed parts of the resist have been removed, or after a pattern transfer step such as etching. The latter possibility limits the possibilities for rework of faulty substrates but may still provide useful information.

Figures 3A, 3B:
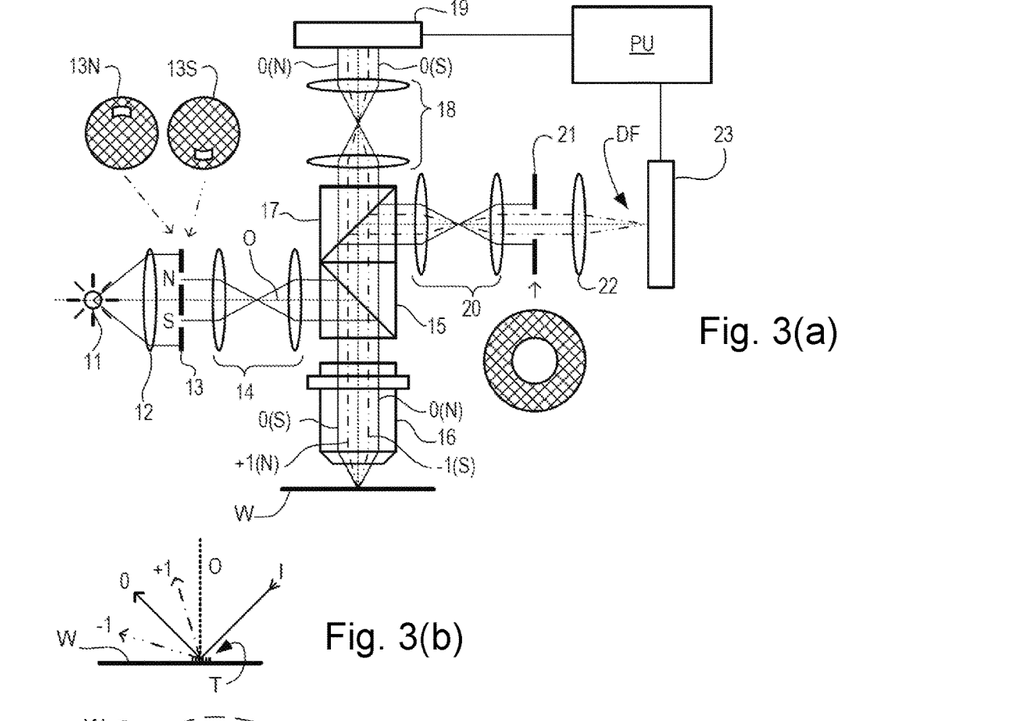
FIGS. 3(a)-3(d) comprise (a) a schematic diagram of a dark field scatterometer for use in measuring targets using a first pair of illumination apertures; (b) a detail of diffraction spectrum of a target grating for a given direction of illumination; (c) a depiction of a known form of multiple grating target and an outline of a measurement spot on a substrate; and (d) a depiction of an image of the target of FIG. 3(c) obtained in the scatterometer of FIG. 3(a)

A metrology apparatus is shown in FIG. 3(a). A target T and diffracted rays of measurement radiation used to illuminate the target are illustrated in more detail in FIG. 3(b). The metrology apparatus illustrated is of a type known as a dark field metrology apparatus. The metrology apparatus may be a stand-alone device or incorporated in either the lithographic apparatus LA, e.g., at the measurement station, or the lithographic cell LC. An optical axis, which has several branches throughout the apparatus, is represented by a dotted line O. In this apparatus, light emitted by source 11 (e.g., a xenon lamp) is directed onto substrate W via a beam splitter 15 by an optical system comprising lenses 12, 14 and objective lens 16. These lenses are arranged in a double sequence of a 4 F arrangement. A different lens arrangement can be used, provided that it still provides a substrate image onto a detector, and simultaneously allows for access of an intermediate pupil-plane for spatial-frequency filtering. Therefore, the angular range at which the radiation is incident on the substrate can be selected by defining a spatial intensity distribution in a plane that presents the spatial spectrum of the substrate plane, here referred to as a (conjugate) pupil plane. In particular, this can be done by inserting an aperture plate 13 of suitable form between lenses 12 and 14, in a plane which is a back-projected image of the objective lens pupil plane. In the example illustrated, aperture plate 13 has different forms, labeled 13N and 13S, allowing different illumination modes to be selected. The illumination system in the present examples forms an off-axis illumination mode. In the first illumination mode, aperture plate 13N provides off-axis from a direction designated, for the sake of description only, as 'north'. In a second illumination mode, aperture plate 13S is used to provide similar illumination, but from an opposite direction, labeled 'south'. Other modes of illumination are possible by using different apertures. The rest of the pupil plane is desirably dark as any unnecessary light outside the desired illumination mode will interfere with the desired measurement signals.

As shown in FIG. 3(b), target T is placed with substrate W normal to the optical axis O of objective lens 16. The substrate W may be supported by a support (not shown). A ray of measurement radiation I impinging on target T from an angle off the axis O gives rise to a zeroth order ray (solid line 0) and two first order rays (dot-chain line +1 and double dot-chain line −1). It should be remembered that with an overfilled small target, these rays are just one of many parallel rays covering the area of the substrate including metrology target T and other features. Since the aperture in plate 13 has a finite width (necessary to admit a useful quantity of light, the incident rays I will in fact occupy a range of angles, and the diffracted rays 0 and +1/−1 will be spread out somewhat. According to the point spread function of a small target, each order +1 and −1 will be further spread over a range of angles, not a single ideal ray as shown. Note that the grating pitches of the targets and the illumination angles can be designed or adjusted so that the first order rays entering the objective lens are closely aligned with the central optical axis. The rays illustrated in FIGS. 3(a) and 3(b) are shown somewhat off axis, purely to enable them to be more easily distinguished in the diagram.

At least the 0 and +1 orders diffracted by the target T on substrate W are collected by objective lens 16 and directed back through beam splitter 15. Returning to FIG. 3(a), both the first and second illumination modes are illustrated, by designating diametrically opposite apertures labeled as north (N) and south (S). When the incident ray I of measurement radiation is from the north side of the optical axis, that is when the first illumination mode is applied using aperture plate 13N, the +1 diffracted rays, which are labeled +1(N), enter the objective lens 16. In contrast, when the second illumination mode is applied using aperture plate 13S the −1 diffracted rays (labeled −1(S)) are the ones which enter the lens 16.

A second beam splitter 17 divides the diffracted beams into two measurement branches. In a first measurement branch, optical system 18 forms a diffraction spectrum (pupil plane image) of the target on first sensor 19 (e.g. a CCD or CMOS sensor) using the zeroth and first order diffractive beams. Each diffraction order hits a different point on the sensor, so that image processing can compare and contrast orders. The pupil plane image captured by sensor 19 can be used for focusing the metrology apparatus and/or normalizing intensity measurements of the first order beam. The pupil plane image can also be used for many measurement purposes such as reconstruction.

In the second measurement branch, optical system 20, 22 forms an image of the target T on sensor 23 (e.g. a CCD or CMOS sensor). In the second measurement branch, an aperture stop 21 is provided in a plane that is conjugate to the pupil-plane. Aperture stop 21 functions to block the zeroth order diffracted beam so that the image of the target formed on sensor 23 is formed only from the −1 or +1 first order beam. The images captured by sensors 19 and 23 are output to processor PU which processes the image, the function of which will depend on the particular type of measurements being performed. Note that the term 'image' is used here in a broad sense. An image of the grating lines as such will not be formed, if only one of the −1 and +1 orders is present.

Figure 3C:
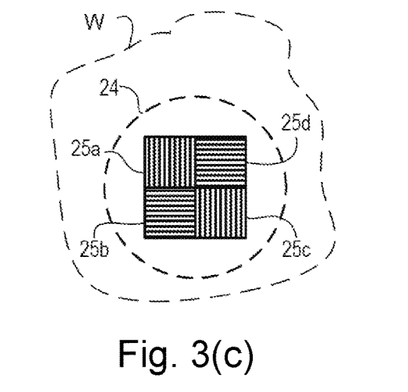
Figure 3D:
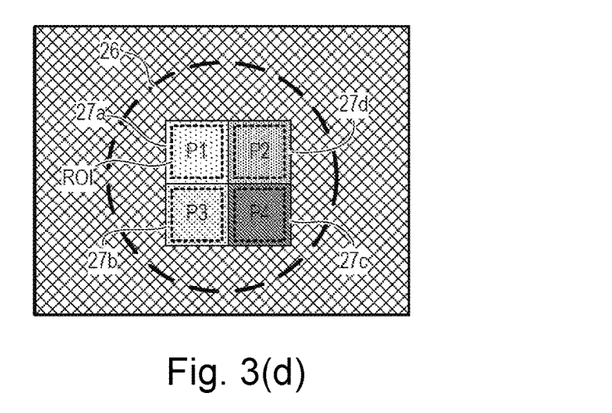

The particular forms of aperture plate 13 and field stop 21 shown in FIG. 3 are purely examples. In another embodiment of the invention, on-axis illumination of the targets is used and an aperture stop with an off-axis aperture is used to pass substantially only one first order of diffracted light to the sensor. In yet other embodiments, $2^{nd}$, $3^{rd}$ and higher order beams (not shown in FIG. 3) can be used in measurements, instead of or in addition to the first order beams.

In order to make the measurement radiation adaptable to these different types of measurement, the aperture plate 13 may comprise a number of aperture patterns formed around a disc, which rotates to bring a desired pattern into place. Note that aperture plate 13N or 13S can only be used to measure gratings oriented in one direction (X or Y depending on the set-up). For measurement of an orthogonal grating, rotation of the target through 90° and 270° might be implemented. The use of these, and numerous other variations and applications of the apparatus are described in prior published applications, mentioned above.

FIG. 3(c) depicts a (composite) target formed on a substrate according to known practice. The target in this example comprises four gratings 25a to 25d positioned closely together so that they will all be within a measurement scene or measurement spot 24 formed by the metrology radiation illumination beam of the metrology apparatus. The four gratings thus are all simultaneously illuminated and simultaneously imaged on sensors 19 and 23. In an example dedicated to measurement of overlay, gratings 25a to 25d are themselves composite gratings formed by overlying gratings that are patterned in different layers of the semi-conductor device formed on substrate W. Gratings 25a to 25d may have differently biased overlay offsets (deliberate mismatch between layers) in order to facilitate measurement of overlay between the layers in which the different parts of the composite gratings are formed. Such techniques are well known to the skilled person and will not be described further. Gratings 25a to 25d may also differ in their orientation, as shown, so as to diffract incoming radiation in X and Y directions. In one example, gratings 25a and 25c are X-direction gratings with biases of the +d, −d, respectively. Gratings 25b and 25d are Y-direction gratings with offsets +d and −d respectively. Separate images of these gratings can be identified in the image captured by sensor 23. This is only one example of a target. A target may comprise more or fewer than four gratings, or only a single grating.

FIG. 3(d) shows an example of an image that may be formed on and detected by the sensor 23, using the target of FIG. 3(c) in the apparatus of FIG. 3(a). While the pupil plane image sensor 19 cannot resolve the different individual gratings 25a to 25d, the image sensor 23 can do so. The dark rectangle represents the field of the image on the sensor, within which the illuminated spot 24 on the substrate is imaged into a corresponding circular area 26. Within this, rectangular areas 27a to 27d represent the images of the small target gratings 25a to 25d. If the targets are located in product areas, product features may also be visible in the periphery of this image field. Image processor and controller PU processes these images using pattern recognition to identify the separate images 27a to 27d of gratings 25a to 25d. In this way, the images do not have to be aligned very precisely at a specific location within the sensor frame, which greatly improves throughput of the measuring apparatus as a whole.

Once the separate images of the gratings have been identified, the intensities of those individual images can be measured, e.g., by averaging or summing selected pixel intensity values within the identified areas. Intensities and/or other properties of the images can be compared with one another. These results can be combined to measure different parameters of the lithographic process. Overlay performance is an important example of such a parameter.

Presently, when performing dark field measurements using the second imaging branch, the measurement radiation used comprises only a single wavelength. The measurement radiation shows different behavior for different layers of the substrate being measured. Therefore, the wavelength of the measurement radiation should be optimized for the layer in which the target being measured is comprised. This means that the measurement radiation needs individual tuning for different measurements of targets in different layers. This takes significant time, while it is always desirable to reduce measurement time to increase fabrication productivity and/or accuracy (by allowing more measurements to be made). In addition, multilayer overlay measurements are sometimes performed, where multiple targets in different layers are captured in a single image. For such multilayer measurements, optimization of wavelength for targets in different layers is not possible, and the wavelength chosen will only be a best compromise for the different targets.

Figure 4:
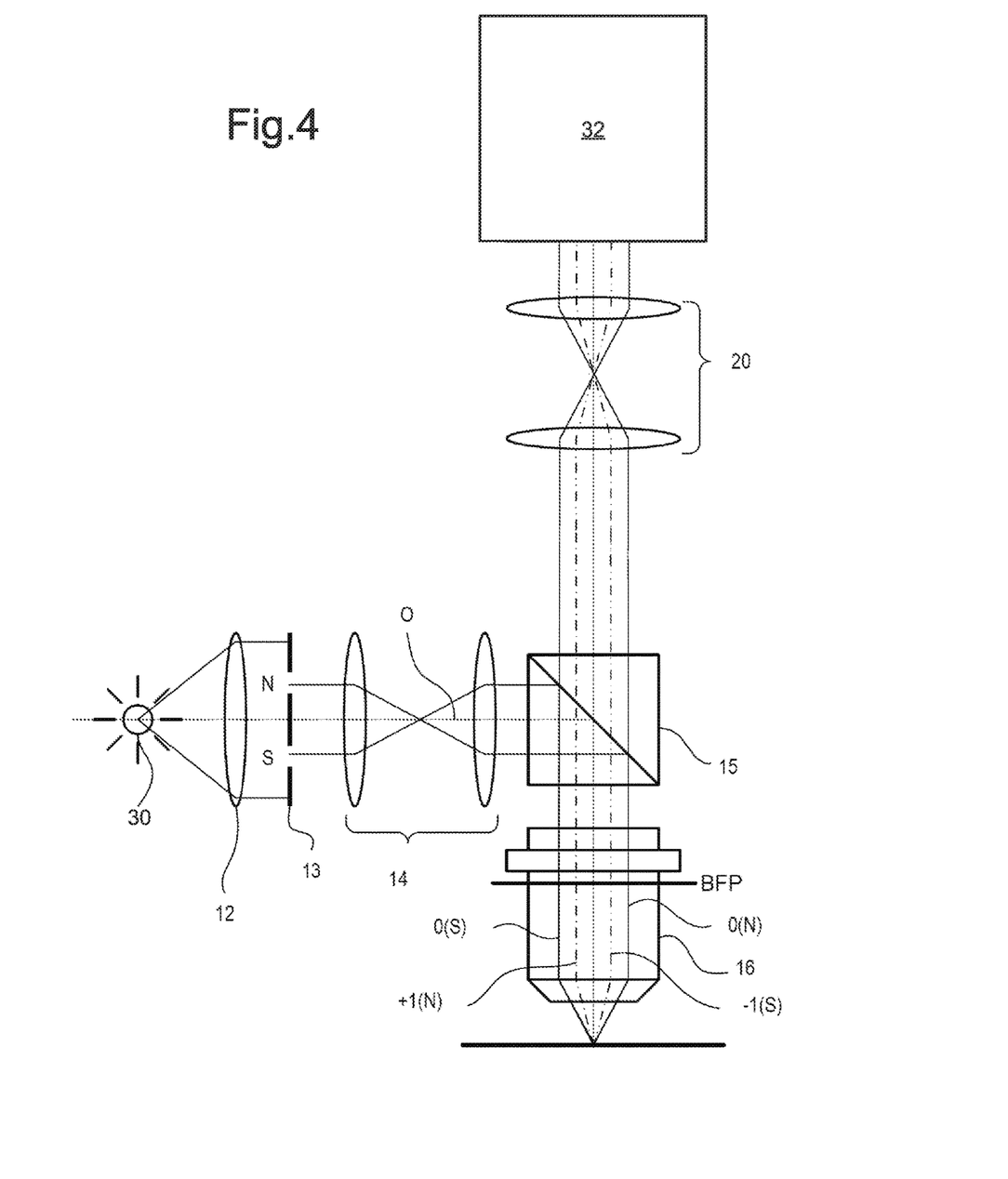
FIG. 4 depicts a metrology apparatus according to an embodiment of the invention.

FIG. 4 schematically illustrates a metrology apparatus architecture which aims to address these issues. It does this by performing measurements on a target (which may be similar to the target depicted in FIG. 3(c) for example) using multiple wavelengths in parallel. The technique used may be referred to as multispectral imaging. This allows selection of the optimal wavelength for each individual layer. Therefore, when performing a multilayer measurement for example, the wavelength can be optimized for each target without sacrificing throughput. Also, the provision of a complete spectral map of a target improves the robustness of the overlay measurement with respect to process variation.

The metrology apparatus is largely the same as that of the metrology apparatus of FIG. 3(a), and in particular the second measurement branch of this apparatus (Apparatuses according to this disclosure may optionally comprise another measurement branch in a similar manner to that illustrated in FIG. 3(a)). As such, the optical design principle between the illumination system and the sensor is largely unchanged, with the same numerals being attributed to equivalent elements.

The main differences between earlier designs and the metrology apparatus of FIG. 4 are illumination system 30 and the inclusion of a multispectral unit 32, in place of sensor 23.

The illumination system 30 provides measurement radiation comprising multiple wavelengths. The measurement radiation may comprise a continuous spectrum or multiple discrete wavelengths (or wavelength bands). In an embodiment, the measurement radiation may comprise multiple wavelengths extending from 400 nm to 900 nm.

FIG. 4 depicts an example of a metrology apparatus for measuring a structure formed on a substrate W by a lithographic process. The four gratings 25a-25d of FIG. 3(c) are examples of structures suitable for measurement by the metrology apparatus. The metrology apparatus comprises an optical system configured to illuminate the structure with measurement radiation and detect the measurement radiation scattered by the structure. The optical system comprises a multispectral unit 32 capable of simultaneously detecting scattered measurement radiation in different wavelength bands.

Figure 5:
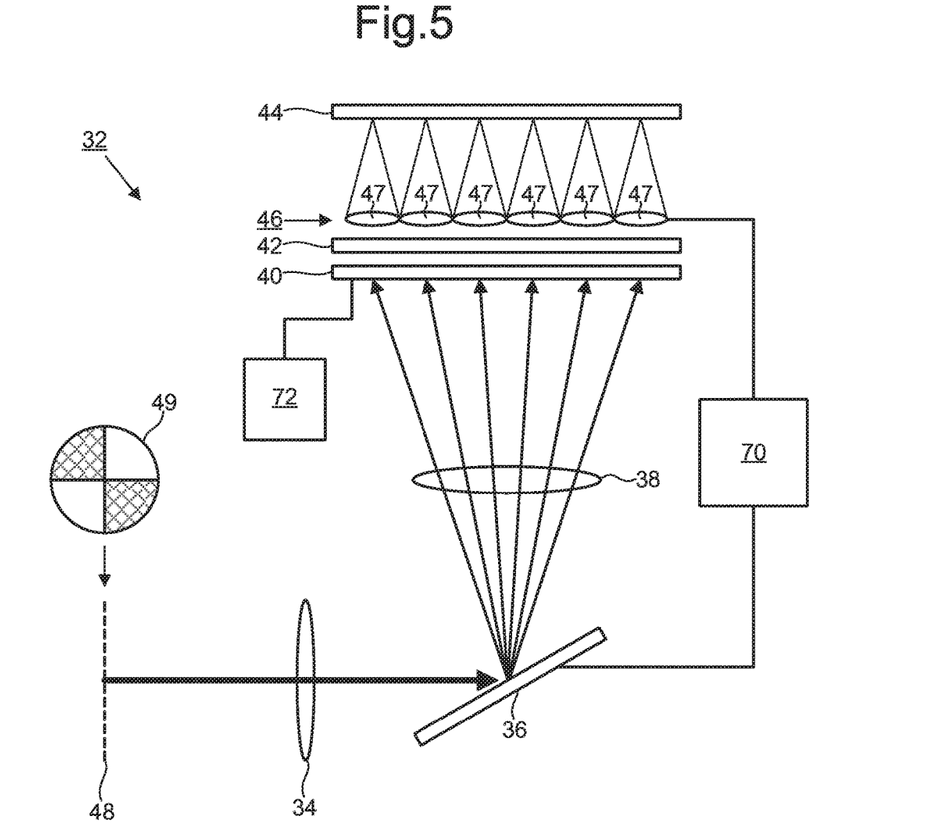
FIG. 5 depicts a multispectral unit comprising an array of lenses, an optical wedge element, a filter system, and a dispersive element.

FIG. 5 depicts an example multispectral unit 32. The multispectral unit 32 comprises an array 46 of lenses 47 and a dispersive element 36.

FIG. 5 schematically depicts propagation of scattered measurement radiation from a pupil plane 48 through to a sensor 44. The pupil plane 48 is a plane in which at least part of a diffraction spectrum of the target is formed (a pupil plane image). A pupil plane image corresponding to a dark field illumination mode containing both first order diffraction beams is depicted schematically and labelled 49. Other illumination modes can be used. Measurement radiation passes from the pupil plane 48 through a lens 34 onto the dispersive element 36. Measurement radiation passes from the dispersive element 36 through a lens 38 onto the sensor 44. In the embodiment shown, the measurement radiation also passes through a filter system 40 and an optical wedge 42, which will be described in further detail below. Lenses 34 and 38 may be configured in a 4 F arrangement.

The array 46 of lenses 47 focuses scattered measurement radiation onto the sensor 44. In an embodiment, the array 46 of lenses 47 comprises a plurality of lenses 47 arranged in a regular 1D or 2D array. In an embodiment the lenses are nominally identical (e.g. same diameter) but may be individually adjustable to allow fine tuning of images formed by the lenses 47 on the sensor 44. For example, in an embodiment the focal length or position of each of the lenses 47 can be individually adjusted. Lenses having individually adjustable focal length or position are well known in the art, so no further details are provided here. Fine tuning of the lenses 47 can compensate for example for variations in the optical properties of the lens as a function of wavelength. As described below, each of the lenses 47 will receive radiation in a different wavelength band relative to other lenses 47. Additionally, each of the lenses 47 may receive radiation in different wavelength bands at different times.

The dispersive element 36 directs scattered measurement radiation in each of a plurality of non-overlapping wavelength bands exclusively onto a different respective lens 47 of the array 46. Thus, for a case where six non-overlapping wavelength bands are provided, a first of the wavelength bands would be directed onto a first lens 47 and no other lens 47, a second of the wavelength bands would be directed onto a second lens 47 and no other lens 47, etc., up to a sixth of the wavelength bands being directed onto a sixth lens 47 and no other lens 47. A non-overlapping wavelength band is a band containing a range of wavelengths that are all outside of all of the other non-overlapping wavelength bands.

The dispersive element 36 may comprise any element which is capable of changing a direction of propagation of a beam of radiation in a manner that is dependent on the wavelength of the radiation. In an embodiment the dispersive element 36 comprises a diffraction grating or a prism.

The dispersive element 36 spatially separates components of the scattered measurement radiation that have different wavelengths (different wavelength bands). The array 46 of lenses 47 focuses (and in this embodiment forms images of the target from) the separated components onto different regions on the sensor 44. This arrangement makes it possible simultaneously to measure the structure from which the measurement radiation has been scattered for a plurality of different wavelength bands. High quality measurements of the structure can therefore be made because the measurements are not restricting to a single wavelength band. The measurement may be made with high efficiency because it is not necessary to perform measurements using different wavelength bands at different times.

In an embodiment, the array 46 of lenses 47 is located in the plane (a pupil plane) in which at least a portion of a pupil plane image of the structure is formed. In the embodiment depicted in FIG. 5 the pupil plane image comprises first order diffraction components only (−1 and +1 order components). In an embodiment each lens 47 in the array 46 forms an image on the sensor 44. As mentioned above, the term "image" is used here in a broad sense. If all diffraction orders were present in the pupil plane the image would be a complete image of the structure scattering the measurement radiation (i.e. including all spatial frequencies). If less than all of the diffraction orders are present the image formed on the sensor 44 will not be a complete image of the structure.

In an embodiment, the array 46 of lenses 47 are configured to correct distortions to the pupil plane image, for example distortions introduced by the dispersive element 36. In an embodiment the array 46 of lenses is configured to correct anomorphic distortions introduced by the dispersive element 36 (which if not corrected would distort circular images to elliptical images). This may be achieved for example by using an array 46 of lenses 47 comprising cylindrical lenses 47.

In an embodiment, an optical wedge element 42 is provided. The optical wedge element 42 spatially separates radiation originating from different diffraction orders in the scattered measurement radiation. The spatial separation is such that radiation from different diffraction orders is detected in different respective non-overlapping regions on the sensor 44. An example optical wedge element 42 is depicted schematically in FIG. 6. An example set of pupil plane images resulting from scattered measurement radiation of different wavelengths is shown superimposed onto an input surface of the optical wedge element 42. The optical wedge element 42 is configured such that a region of each pupil plane image corresponding to −1 first order radiation (e.g. approximately a top right quadrant) is incident on a region of the optical wedge element 42 (e.g. an upper region of the optical wedge element 42 in the orientation shown in FIG. 6) which redirects radiation at a first angle and a region of each pupil plane image corresponding to +1 first order radiation (e.g. approximately a bottom left quadrant) is incident on a region of the optical wedge element 42 (e.g. lower region in the orientation of FIG. 6) which redirects radiation at a second angle, different to the first angle. The optical wedge element 42 separates images from different diffraction orders (e.g. −1 and −1) on the sensor 44, thereby allowing different diffraction orders to be measured simultaneously. An alternative approach for measuring different diffraction orders would be to change the illumination mode, for example by changing the aperture plate 13. In this way the multispectral unit 32 could receive −1 first order radiation and +1 first order radiation at different times. This approach would normally be more time-consuming however than measuring the different diffraction orders simultaneously using the optical wedge element 42.

Figures 7A, 7B, 7C:
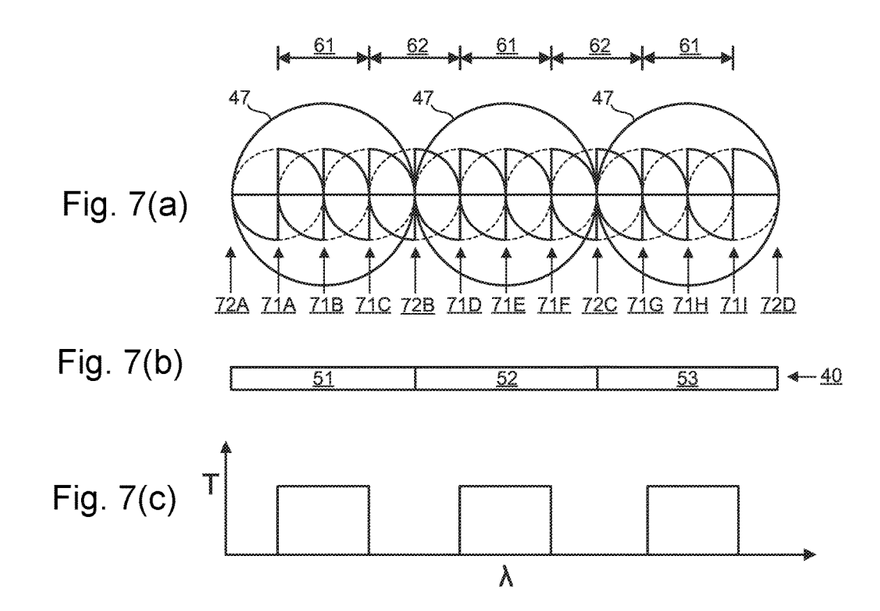
FIGS. 7(a)-7(c) comprise (a) a schematic diagram of three lenses of an array of lenses with representative pupil plane images superimposed therein; (b) example bandpass filters aligned with the three lenses; and (c) a variation of transmittance with wavelength of a filter system.

It is desirable to prevent scattered measurement radiation being incident on the array 46 of lenses 47 in such a way that a pupil plane image overlaps any two of the lenses 47. If this occurs, some of the spatial information necessary to form a high quality image will be split between two different images, thereby corrupting both of those images. In an embodiment, a filter system 40 is provided that filters out bands of wavelengths which would cause such overlap. FIG. 7 depicts an example arrangement.

FIG. 7(a) depicts three example lenses 47 from an array of lenses 46. Superimposed on the three lenses are 11 schematic pupil plane images, equally spaced relative to each other from left to right. Each of the pupil plane images comprises an upper right quadrant and a lower right quadrant containing radiation representing portions of a diffraction pattern of the structure, while the upper left quadrant and lower right quadrant represent portions of the diffraction pattern of the structure that have been blocked. In the case where the measurement radiation output from the dispersive element comprises a continuous range of wavelengths that (in the absence of a filter system 40) would be spread continuously across the three lenses 47, a continuous spread of pupil plane images would also be spread across the three lenses 47. FIG. 7 shows only eleven representative pupil plane images for ease of explanation.

Nine of the pupil plane images, centered at positions 71A-71I, fall entirely within one and only one of the lenses 47. Two of the pupil plane images, centered at positions 72B and 72C, overlap two different lenses 47 and would therefore contribute radiation to two different images on the sensor 44. All pupil plane images (not shown) that would be centered within half a pupil plane image diameter of the positions 72B and 72C (i.e. anywhere in the range from 71C to 71D or from 71F to 71G, corresponding to the ranges marked 62) would also overlap two different lenses 46. The filter system 40 filters out at least components of the measurement radiation that correspond to these ranges of positions of the pupil plane images. In the geometry shown in FIG. 7, the filter system 40 thus filters out components of the measurement radiation that would produce pupil plane images centered at any position in the ranges marked 62. Conversely, the filter system 40 passes components of the measurement radiation that would produce pupil plane images centered at any position in the ranges marked 61.

In an embodiment, the filter system 40 comprises an array of bandpass filters 51-53, as depicted schematically in FIG. 7(b). Each bandpass filter 51-53 selectively passes radiation within a predetermined band and is aligned with the array 46 of lenses 47 to prevent scattered measurement radiation being incident on the array 46 in such a way that a pupil plane image overlaps any two of the lenses 47. Thus, in the example shown, bandpass filter 51 passes radiation in a wavelength band corresponding to pupil plane images centered in the range from 71A to 71C and blocks all other wavelengths. Bandpass filter 52 passes radiation in a wavelength band corresponding to pupil plane images centered in the range 71D to 71F and blocks all other wavelengths. Bandpass filter 53 passes radiation in a wavelength band corresponding to pupil plane images centered in the range 71G to 71I and blocks all other wavelengths. The overall transmission characteristics of the array of bandpass filters 51-53 is depicted in FIG. 7(c). Transmission T is relatively high (e.g. substantially 100%) for wavelengths providing pupil plane images that are centered in the ranges 61 and relatively low (e.g. substantially zero) for wavelengths providing pupil plane images that are centered in ranges 62.

Figure 6:
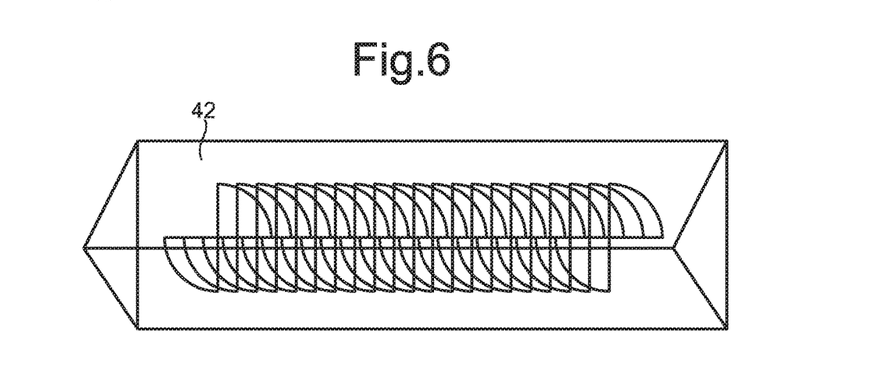
FIG. 6 depicts spatial separation of different diffraction orders using an optical wedge element.

The filter system 40 of FIGS. 6 and 7 is provided in close proximity to the array of lenses 46. This approach is advantageous because the dispersive element 36 has already spread out different wavelength components of the scattered measurement radiation, which facilities the filtering process. For example, as described above, individual bandpass filters can operate on a narrower range of wavelengths than might be the case if the different wavelength components had not been spread. It is not however essential to provide the filter system 40 in this location. As long as the required transmission profile is achieved, for example as depicted in FIG. 7(c), the filtering can occur anywhere in the metrology system. Alternatively or additionally, the illumination system 30 itself may be configured directly to provide a plurality of non-overlapping wavelength bands that are selected such that none of the scattered measurement radiation is incident on the array 46 of lenses 47 in such a way that a pupil plane image overlaps any two of the lenses 47. Thus, in this case the non-overlapping wavelength bands provided by the illumination system 30 would already be spaced apart from each other with substantially no measurement radiation in any wavelength band in between any pair of the plurality of the non-overlapping wavelength bands that would cause a pupil plane image to overlap any two of the lenses 47. In this case no filter system 40 would be necessary.

To provide good sampling in wavelength space it is desirable to arrange for the diameter of the pupil plane image (or width of the pupil plane image parallel to a direction along which lenses 47 of the array 46 are aligned) to be near 50% of the diameter of each lens 47 of the array 46 (as shown in FIG. 7), for example 25%-50% of the diameter, optionally 33%-50% of the diameter, optionally substantially 50% of the diameter. Specific parameters of an example metrology apparatus are described below.

The following parameters would be applicable to the case where it is desired to measure a structure using measurement radiation spread over a total bandwidth of $\Delta\lambda=100$ nm with a wavelength resolution of $\delta\lambda=10$ nm. Thus, each lens 47 acquires radiation (and forms an image on the sensor 44) over a 10 nm bandwidth and multiple measurements of the same bandwidth are performed in parallel over a 100 nm range. In such a case the diameter $D_p$ of a pupil plane image for a typical optical system would be about 3.8 mm. For a dispersive element 36 comprising a diffraction grating with a pitch P=500 nm, the diffracted angle would be given by $=\sin^{-1}(\lambda/P)$. To achieve a spectral resolution of $\delta\lambda=10$ nm, a focal length f of the lenses 34 and 38 is needed that ensures the lateral displacement of the range of wavelengths $\delta\lambda=10$ nm is equal to a diameter of the pupil plane image (i.e. providing the duty cycle shown in FIG. 7(c)). The focal length therefore needs to satisfy $f=D_p P/\delta\lambda$, which yields f=10 cm. Using this focal length it is possible to calculate the total physical size of the dispersed pupil plane images (the length of the spread of pupil plane images across the array 46) and thus the required size of the array 46, as well as of the sensor 44 that will receive images from the array 46.

The total spatial extent of the dispersed pupil image is approximately $L=f \Delta\lambda/P$. This gives the size of the array 46 (and sensor 44) as L=3.8 cm. For a 70× magnification, the focal length of the lenses 47 would be about 14 cm. For the pupil plane image diameter of 3.8 mm the diameter of each of the lenses 47 should be 7.6 mm. For a total bandwidth $\Delta\lambda=100$ nm, five lenses 47 would be needed in the array 46, each lens 47 measuring a bandwidth of $\delta\lambda=10$ nm. Thus, this configuration allows for the measurement of the structure (e.g. to obtain an overlay offset) at five equidistant wavelength bands of 10 nm width and 10 nm separation between them. For measuring a different wavelength range, the dispersive element 36 (in this case a diffraction grating) would need to be adjusted (e.g. rotated) or the lens array 46 and possibly also the sensor 44 would need to be moved. Additionally, any array of bandpass filters 40 that is used may also need to be moved or replaced so that the appropriate wavelength bands are allowed through the respective lenses 47 of the array 46.

High quality imaging using the metrology apparatus depends on appropriate alignment of the array 46 of lenses 47 and the dispersive element 36. In an embodiment an alignment controller 70 is provided to allow the relative alignment between at least the array 46 of lenses 47 and the dispersive element 36 to be controlled. The required relative alignment will in general depend on the particular range of wavelengths covered by the plurality of non-overlapping wavelength bands being used. In an embodiment, different pluralities of overlapping wavelength bands may be used.

For example, a first plurality of wavelength bands which are all contained within a first wavelength range may be used, followed by a second plurality of wavelength bands which are all contained with a second wavelength range may be used. The first and second wavelength ranges may themselves be non-overlapping. In this way it is possible to build up a detailed set of measurements of the structure with high spectral resolution over a wide range of wavelengths. Each of the different pluralities of wavelengths will however normally require a different relative alignment at least between the array 46 of lenses 47 and the dispersive element 36 to ensure that each non-overlapping band is aligned appropriately with one of the lens 47 (e.g. such that a pupil plane image does not overlap between the lens 47 and any other lens 47).

In an embodiment, the metrology apparatus further comprises an alignment actuator 70 configured to adjust a position, an orientation, or a position and orientation, of either or both of the array of lenses 46 and the dispersive element 36. The alignment actuator 70 allows the metrology apparatus to selectively switch from a first alignment state to a second alignment state (and optionally one or more further alignment states, as required). The first alignment state is such that scattered measurement radiation in each of a first plurality of non-overlapping wavelength bands is directed exclusively onto a different respective lens 47 of the array 46 of lenses 47. The second alignment state is such that scattered measurement radiation in each of a second plurality of non-overlapping wavelength bands is directed exclusively onto a different respective lens 47 of the array 46 of lenses 47. The first plurality of non-overlapping wavelength bands is different to the second plurality of non-overlapping wavelength bands.

In an embodiment, the alignment actuator 70 adjusts an orientation of the dispersive element 36 by rotating the dispersive element 36.

In an embodiment, the operation of the filter system 40 may also need to be modified in response to a change in the plurality of non-overlapping wavelength bands that is to be measured. In an embodiment a filter system actuator 72 is provided that modifies operation of the filter system 40 in response to a switch from the first alignment state to the second alignment state by the alignment actuator 70. In an embodiment, the operation of the filter system 40 is modified by changing an alignment of an array of bandpass filters relative to the array of lenses 46. In an embodiment the array of bandpass filter is placed on a moveable stage to allow the adjustment. In an embodiment, an array of bandpass filters covering the entire operating spectral range of the metrology apparatus is provided (with an appropriate portion of the array of bandpass filters being aligned with the array 46 of lenses 47 during each measurement process, in accordance with the particular range of wavelengths being measured). In an alternative embodiment, the operation of the filter system 40 is modified by replacing a first array of bandpass filters with a second array of bandpass filters.

Any required adjustment of the array 46 of lenses 47, the dispersive element 36, the sensor 44, and/or the filter system 40 will be carried out prior to measurement of the structure, during a setup phase. No moving parts are required during the measurement of the structure.

The concepts described herein can be used to enable parallel readout of a multispectral measurement instead of having to select each wavelength separately and perform multiple measurements in series. Such measurements may be used, for example, in performing overlay measurements on overlay targets.

Having parallel measurements with different wavelengths make the measurements more robust. For example, better asymmetry correction can be obtained by combining multiple colors (e.g. by using blind source separation techniques).

The concepts disclosed herein may find utility beyond post-lithography measurement of structures for monitoring purposes. For example, such a detector architecture may be used in future alignment sensor concepts that are based on pupil plane detection, used in lithographic apparatuses for aligning the substrate during the patterning process.

While the targets described above are metrology targets specifically designed and formed for the purposes of measurement, in other embodiments, properties may be measured on targets which are functional parts of devices formed on the substrate. Many devices have regular, grating-like structures. The terms 'target grating' and 'target' as used herein do not require that the structure has been provided specifically for the measurement being performed.

The metrology apparatus can be used in a lithographic system, such as the lithographic cell LC discussed above with reference to FIG. 2. The lithographic system comprises a lithographic apparatus LA that performs a lithographic process. The lithographic apparatus may be configured to use the result of a measurement by the metrology apparatus of a structure formed by the lithographic process when performing a subsequently lithographic process, for example to improve the subsequent lithographic process.

An embodiment may include a computer program containing one or more sequences of machine-readable instructions describing methods of measuring targets on a structures and/or analyzing measurements to obtain information about a lithographic process. There may also be provided a data storage medium (e.g., semiconductor memory, magnetic or optical disk) having such a computer program stored therein. Where an existing lithography or metrology apparatus is already in production and/or in use, the invention can be implemented by the provision of updated computer program products for causing a processor to perform the methods described herein.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens," where the context allows, may refer to any one or combination of various types of optical components, including refractive, reflective, magnetic, electromagnetic, and electrostatic optical components.

Further embodiments according to the present invention are further described in below numbered clauses:

1. A metrology apparatus for measuring a structure formed on a substrate by a lithographic process, the metrology apparatus comprising:
   an optical system configured to illuminate the structure with measurement radiation and detect the measurement radiation scattered by the structure, the optical system comprising:
   an array of lenses configured to focus the scattered measurement radiation onto a sensor; and
   a dispersive element configured to direct scattered measurement radiation in each of a plurality of non-overlapping wavelength bands exclusively onto a different respective lens of the array of lenses.

2. The metrology apparatus of clause 1, wherein the array of lenses is located in a plane in which pupil plane images of the structure are formed.

3. The metrology apparatus of clause 2, further comprising a filter system configured to prevent scattered measurement radiation being incident on the array of lenses in such a way that a pupil plane image overlaps any two of the lenses in the array of lenses.

4. The metrology apparatus of clause 3, wherein the filter system comprise an array of bandpass filters aligned with the array of lenses.

5. The metrology apparatus of clause 3 or 4, wherein a diameter of pupil plane images formed at the array of lenses is 25%-50% of the diameter of each lens of the array of lenses.

6. The metrology apparatus of any preceding clause, further comprising an alignment actuator configured to adjust a position, an orientation, or a position and orientation, of either or both of the array of lenses and the dispersive element, in order to selectively switch from a first alignment state to a second alignment state, wherein:
   in the first alignment state scattered measurement radiation in each of a first plurality of non-overlapping wavelength bands is directed exclusively onto a different respective lens of the array of lenses; and
   in the second alignment state scattered measurement radiation in each of a second plurality of non-overlapping wavelength bands is directed exclusively onto a different respective lens of the array of lenses, the first plurality of non-overlapping wavelength bands being different to the second plurality of non-overlapping wavelength bands.

7. The metrology apparatus of clause 6, wherein the alignment actuator is configured to adjust an orientation of the dispersive element by rotating the dispersive element.

8. The metrology apparatus of clause 6 or 7, comprising:
   a filter system configured to prevent scattered measurement radiation being incident on the array of lenses in such a way that a pupil plane image overlaps any two or more of the lenses in the array of lenses; and
   a filter system actuator configured to modify operation of the filter system in response to a switch from the first alignment state to the second alignment state by the alignment actuator.

9. The metrology apparatus of clause 8, wherein the modification of operation of the filter system comprises changing an alignment of an array of bandpass filters relative to the array of lenses.

10. The metrology apparatus of clause 8 or 9, wherein the modification of operation of the filter system comprises replacing a first array of bandpass filters with a second array of bandpass filters.

11. The metrology apparatus of any preceding clause, wherein the dispersive element comprises a diffraction grating or prism.

12. The metrology apparatus of any preceding clause, wherein the array of lenses comprises a plurality of lenses arranged in a regular array.

13. The metrology apparatus of any preceding clause, wherein the array of lenses comprises a plurality of cylindrical lenses.

14. The metrology apparatus of any preceding clause, further comprising an optical wedge element configured to spatially separate radiation originating from different diffraction orders in the scattered measurement radiation such that radiation from different diffraction orders is detected in different respective non-overlapping regions on the sensor.

15. The metrology apparatus of any preceding clause, further comprising a radiation source configured to illuminate the structure with measurement radiation comprising the plurality of non-overlapping wavelength bands and not comprising any wavelength band in between any pair of the plurality of the non-overlapping wavelength bands that would cause a pupil plane image to overlap any two of the lenses in the array of lenses.

16. A lithographic system comprising:
   a lithographic apparatus configured to perform a lithographic process; and
   the metrology apparatus of any preceding clause, wherein:
   the lithographic apparatus is arranged to use the result of a measurement by the metrology apparatus of a structure formed by the lithographic process when performing a subsequent lithographic process.

17. A method of measuring a structure formed on a substrate by a lithographic process, comprising:
   illuminating the structure with measurement radiation comprising at least a plurality of non-overlapping wavelength bands;
   using a dispersive element to spectrally disperse the measurement radiation after scattering of the measurement radiation by the structure in order to direct scattered measurement radiation from each of the plurality of non-overlapping wavelength bands exclusively onto a different respective lens of an array of lenses; and
   detecting radiation from each lens of the array of lenses on a sensor.

18. The method of clause 17, further comprising adjusting a position, an orientation, or a position and orientation, of either or both of the array of lenses and the dispersive element, in order to selectively switch from a first alignment state to a second alignment state, wherein:
in the first alignment state scattered measurement radiation in each of a first plurality of non-overlapping wavelength bands is directed exclusively onto a different respective lens of the array of lenses; and
in the second alignment state scattered measurement radiation in each of a second plurality of non-overlapping wavelength bands is directed exclusively onto a different respective lens of the array of lenses, the first plurality of non-overlapping wavelength bands being different to the second plurality of non-overlapping wavelength bands.

19. The method of clause 18, further comprising:
using a filter system to prevent scattered measurement radiation being incident on the array of lenses in such a way that a pupil plane image overlaps any two of the lenses in the array of lenses; and
modifying operation of the filter system in response to the switch from the first alignment state to the second alignment state.

20. The method of clause 19, wherein the modification of operation of the filter system comprises changing an alignment of an array of bandpass filters relative to the array of lenses.

21. The method of clause 19 or 20, wherein the modification of operation of the filter system comprises replacing a first array of bandpass filters with a second array of bandpass filters.

22. The method of any of clauses 17-21, further comprising spatially separating radiation originating from different diffraction orders in the scattered measurement radiation such that radiation from different diffraction orders is detected in different non-overlapping regions on the sensor.

23. The method of any of clauses 17-22, wherein the structure is illuminated with measurement radiation comprising the plurality of non-overlapping wavelength bands and not comprising any wavelength band in between any pair of the plurality of the non-overlapping wavelength bands that would cause a pupil plane image to overlap any two of the lenses in the array of lenses.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:
1. A metrology apparatus for measuring a structure formed on a substrate by a lithographic process, the metrology apparatus comprising:
an optical system configured to illuminate the structure with measurement radiation and detect the measurement radiation scattered by the structure, the optical system comprising:
an array of lenses configured to focus the scattered measurement radiation onto a sensor; and
a dispersive element configured to direct scattered measurement radiation in each of a plurality of non-overlapping wavelength bands exclusively onto a different respective lens of the array of lenses.

2. The metrology apparatus of claim 1, wherein the array of lenses is located in a plane that pupil plane images of the structure are formed.

3. The metrology apparatus of claim 2, further comprising a filter system configured to prevent scattered measurement radiation from being incident on the array of lenses in such a way that a pupil plane image overlaps any two of the lenses in the array of lenses.

4. The metrology apparatus of claim 3, wherein the filter system comprises an array of bandpass filters aligned with the array of lenses.

5. The metrology apparatus of claim 3, wherein a diameter of pupil plane images formed at the array of lenses is 25%-50% of the diameter of each lens of the array of lenses.

6. The metrology apparatus of claim 1, further comprising an alignment actuator configured to adjust a position, an orientation, or a position and orientation, of either or both of the array of lenses and the dispersive element, in order to selectively switch from a first alignment state to a second alignment state, wherein:
in the first alignment state scattered measurement radiation in each of a first plurality of non-overlapping wavelength bands is directed exclusively onto a different respective lens of the array of lenses; and
in the second alignment state scattered measurement radiation in each of a second plurality of non-overlapping wavelength bands is directed exclusively onto a different respective lens of the array of lenses, the first plurality of non-overlapping wavelength bands being different than the second plurality of non-overlapping wavelength bands.

7. The metrology apparatus of claim 6, wherein the alignment actuator is configured to adjust an orientation of the dispersive element by rotating the dispersive element.

8. The metrology apparatus of claim 6, comprising:
a filter system configured to prevent scattered measurement radiation from being incident on the array of lenses in such a way that a pupil plane image overlaps any two or more of the lenses in the array of lenses; and
a filter system actuator configured to modify operation of the filter system in response to a switch from the first alignment state to the second alignment state by the alignment actuator.

9. The metrology apparatus of claim 8, wherein the modification of operation of the filter system comprises changing an alignment of an array of bandpass filters relative to the array of lenses.

10. The metrology apparatus of claim 8, wherein the modification of operation of the filter system comprises replacing a first array of bandpass filters with a second array of bandpass filters.

11. The metrology apparatus of claim 1, further comprising an optical wedge element configured to spatially separate radiation originating from different diffraction orders in the scattered measurement radiation, such that radiation from different diffraction orders is detected in different respective non-overlapping regions on the sensor.

12. The metrology apparatus of claim 1, further comprising a radiation source configured to illuminate the structure with measurement radiation comprising the plurality of non-overlapping wavelength bands and not comprising any wavelength band in between any pair of the plurality of the non-overlapping wavelength bands that would cause a pupil plane image to overlap any two of the lenses in the array of lenses.

13. A lithographic system comprising:
a lithographic apparatus configured to perform a lithographic process; and
the metrology apparatus measuring a structure formed on a substrate by the lithographic process, the metrology apparatus comprising:
an optical system configured to illuminate the structure with measurement radiation and detect the measurement radiation scattered by the structure, the optical system comprising:
an array of lenses configured to focus the scattered measurement radiation onto a sensor; and
a dispersive element configured to direct scattered measurement radiation in each of a plurality of non-overlapping wavelength bands exclusively onto a different respective lens of the array of lenses, wherein:
the lithographic apparatus is arranged to use the result of a measurement by the metrology apparatus of a structure formed by the lithographic process when performing a subsequent lithographic process.

14. A method of measuring a structure formed on a substrate by a lithographic process, comprising:
illuminating the structure with measurement radiation comprising at least a plurality of non-overlapping wavelength bands;
spectrally dispersing the measurement radiation, using a dispersive element, after scattering of the measurement radiation by the structure in order to direct scattered measurement radiation from each of the plurality of non-overlapping wavelength bands exclusively onto a different respective lens of an array of lenses; and
detecting radiation from each lens of the array of lenses onto respective portions of a sensor.

15. The method of claim 14, further comprising:
adjusting a position, an orientation, or a position and orientation, of either or both of the array of lenses and the dispersive element, in order to selectively switch from a first alignment state to a second alignment state, wherein:
in the first alignment state, scattered measurement radiation in each of a first plurality of non-overlapping wavelength bands is directed exclusively onto a different respective lens of the array of lenses; and
in the second alignment state, scattered measurement radiation in each of a second plurality of non-overlapping wavelength bands is directed exclusively onto a different respective lens of the array of lenses, the first plurality of non-overlapping wavelength bands being different to the second plurality of non-overlapping wavelength bands.

16. The method of claim 15, further comprising:
preventing, using a filter system, scattered measurement from radiation being incident on the array of lenses in such a way that a pupil plane image overlaps any two of the lenses in the array of lenses; and
modifying operation of the filter system in response to the switch from the first alignment state to the second alignment state.

17. The method of claim 16, wherein the modification of operation of the filter system comprises changing an alignment of an array of bandpass filters relative to the array of lenses.

18. The method of claim 16, wherein the modification of operation of the filter system comprises replacing a first array of bandpass filters with a second array of bandpass filters.

19. The method of claim 14, further comprising spatially separating radiation originating from different diffraction orders in the scattered measurement radiation, such that radiation from different diffraction orders is detected in different non-overlapping regions on the sensor.

20. The method of claim 14, wherein the structure is illuminated with measurement radiation comprising the plurality of non-overlapping wavelength bands and not comprising any wavelength band in between any pair of the plurality of the non-overlapping wavelength bands that would cause a pupil plane image to overlap any two of the lenses in the array of lenses.

* * * * *